United States Patent [19]

Nagatomo et al.

[11] Patent Number: 5,023,052

[45] Date of Patent: Jun. 11, 1991

[54] ELEMENT FOR ANALYZING BODY FLUIDS

[75] Inventors: Shigeru Nagatomo; Mitsutoshi Tanaka, both of Saitama, Japan

[73] Assignee: Fuji Photo Film Co., Ltd., Kanagawa, Japan

[21] Appl. No.: 300,123

[22] Filed: Jan. 23, 1989

[30] Foreign Application Priority Data

Jan. 20, 1988 [JP] Japan .................................. 63-10452

[51] Int. Cl.$^5$ ........................................... G01N 31/22
[52] U.S. Cl. ......................................... 422/56; 422/57; 422/58; 435/7.1; 435/805; 435/7.92; 436/169; 436/170; 436/518
[58] Field of Search ........................... 422/56, 57, 58; 436/169, 170; 435/805, 7

[56] References Cited

U.S. PATENT DOCUMENTS

| | | | |
|---|---|---|---|
| 4,600 | 3/1989 | Tanaka et al. | 422/57 |
| 3,992,158 | 11/1976 | Przybylowicz et al. | 422/58 |
| 4,042,335 | 8/1977 | Clément | 422/56 |
| 4,166,093 | 8/1979 | Smith-Lewis et al. | 422/56 |
| 4,292,272 | 9/1981 | Kitajima et al. | 422/57 |
| 4,472,498 | 9/1984 | Masuda et al. | 422/57 |
| 4,576,793 | 3/1986 | Koyama et al. | 422/56 |
| 4,786,595 | 11/1988 | Arai et al. | 422/56 |
| 4,870,005 | 9/1989 | Akiyoshi et al. | 422/56 |

FOREIGN PATENT DOCUMENTS 0123443 10/1984 European Pat. Off. .............. 422/57

*Primary Examiner*—David L. Lacey
*Assistant Examiner*—Jill Johnston
*Attorney, Agent, or Firm*—McAulay Fisher Nissen Goldberg & Kiel

[57] ABSTRACT

A multi-layer analytical element for analyzing body fluids includes a light transmitting and water impermeable support having provided thereon a fist non-fibrous porous layer, a second non-fibrous porous layer, and a fibrous porous layer in this order, the three porous layers being bonded together in one piece with an adhesive locally applied in such a manner that small through-holes are formed so as not to substantially interfere with uniform penetration of the liquid. At least one of the non-fibrous porous layers contains a reagent composition which undergoes a detectable optical change in the presence of a component to be analyzed, which optical change is detectable in the first non-fibrous porous layer, and wherein the non-fibrous porous layer comprises polysulfone. The analytical element enables dry analyses with improved precision independently of the hematocrit value of samples.

16 Claims, 1 Drawing Sheet

ELEMENT FOR ANALYZING BODY FLUIDS

FIELD OF THE INVENTION

This invention relates to an element for dry chemical analyses useful for quantitative determination of a specific substance in body fluids, such as blood.

BACKGROUND OF THE INVENTION

Quantitative analyses of various metabolities in body fluids, e.g., glucose, bilirubin, urea nitrogen, uric acid, cholesterol, lactate dehydrogenase, creatine kinase, GOT, GPT, etc., are of clinical significance and inevitable for the diagnosis, tracing of therapeutic progress, and prognostic judgement of disease. In clinical chemical examinations of body fluid samples, such as blood, it is desirable to make a precise analysis with a small amount of a liquid sample. A wet process using an analytical reagent in the form of a solution has hitherto been widely employed in this field, but it lacks the rapidity required for such analysis.

A dry chemical analysis using an analytical element in a substantially dry state is also known, in which a testing element or multi-layer analytical element having an analytical reagent system incorporated therein is used. The dry chemical analysis is superior to the wet chemical analysis in convenience, economy, and rapidness.

A dry multi-layer analytical element has been developed which allows a highly precise analysis to be conducted with a small amount of a liquid sample. Known dry multi-layer analytical elements include those disclosed in JP-B-53-21677 (the term "JP-B" as used herein means an "examined published Japanese patent application") and JP-A-164356 and 60-222769 (the term "JP-A" as used herein means as unexamined published Japanese patent application"). In one instance, a dry multi-layer analytical element is composed of a transparent support, a reagent layer, a reflective layer, and a developing layer. The transparent support is, for example, a thin plastic film which has been subjected to a subbing treatment. The reagent layer provided on the transparent support contains a reagent which reacts with a substance to be analyzed (analysis) to develop a color having an optical density corresponding to the amount of the substance under analysis. The reflective layer serves to prevent light transmitted through the reagent layer from reaching the spreading layer and to exclude the influence of a liquid sample remaining in the spreading layer on the optical measurement of the reagent layer. The spreading layer functions to spread a liquid sample dropwise added to an area substantially in proportion to the amount of the sample added. Quantitative analysis by the use of such a dry analytical element can be carried out by dropping a given amount of a liquid sample, e.g., whole blood, on the surface of the spreading layer, where the blood is spread over. The blood then passes through the reflective layer and reaches the reagent layer, where it reacts with a reagent to develop a color. After the dropwise addition of the sample, the analytical element is preserved at a constant temperature for an appropriate period of time to allow sufficient progress of the color development. Thereafter, light is irradiated on the element from the side of the transparent support, and the amount of the reflected light is measured at a specific wavelength to obtain a reflection density, from which the amount of the analysis can be obtained using a previously prepared calibration curve.

In either the wet and dry chemical analyses, it has been usual to use, as a sample, the serum or plasma prepared by separating red blood cells from whole blood. However, separation of red blood cells from the other blood components is laborious and requires cost by equipment. It is therefore desirable to make the analysis using undiluted whole blood.

In dry chemical analyses on whole blood, it is necessary to separate the blood cells, i.e., the red blood cells and white blood cells, and other high-molecular-weight components of the whole blood by a means provided within the analytical element. It has been proposed to separate the blood cells and high-molecular-weight components from the whole blood by means of a filter layer provided in an analytical element as disclosed in JP-B-53-21677. Nevertheless, as mentioned in JP-A-60-111960, it requires substantial time to remove the blood cells from serum or plasma by means of such a filter layer. Moreover, it is possible a part of the analysis may be lost during passage through the filter layer, causing errors in the analysis.

JP-A-60-279860 proposes a dry analytical element useful for analyzing a specific component in a whole blood sample, in which blood cells are separated and removed from the plasma within an analytical element and the component to be analyzed can be rapidly diffused into a reagent layer. This analytical element has a multi-layer structure comprising, in this order, a support, a first non-fibrous porous layer, a second non-fibrous porous layer, and a fibrous porous layer; the three layers being intimately bonded together in once piece with an adhesive locally applied between each adjacent surface so as not to substantially interfere with uniform penetration of a liquid sample therethrough. Any one of the three layers may contain a reagent composition which develops a color and the second non-fibrous porous layer has an average effective pore size of from 0.8 to 30 $\mu$m.

However, when whole blood is analyzed with the multi-layer analytical element, the spectral absorption of the color developed by the reagent composition may be influenced by the amount of the sample added or diffusion in the developing layer. This is particularly so when the wavelength used for detection is close to the absorption wavelength of the hemoglobin in blood. Additionally, empirical results have shown that, with the same analyte content in the plasma, the analytical results vary depending on the hematocrit value (the volume percentage of blood cells in whole blood).

SUMMARY OF THE INVENTION

One object of this invention is to provide a dry analytical element for analyzing a specific component in a whole blood sample, in which the blood cells in the whole blood are separated from the blood plasma to avoid interference by red blood cells and the component to be analyzed in the plasma can be rapidly diffused into a reagent layer, to thereby give a highly precise result irrespective of the hematocrit value of the blood.

It has now been found that this object can be accomplished by a multi-layer analytical element comprising, in this order, a light transmitting and water impermeable support, a first non-fibrous porous layer, a second non-fibrous porous layer, and a fibrous porous layer, the three porous layers being bonded together in one piece with an adhesive locally applied between each adjacent surface so as not to substantially interfere with uniform penetration of a liquid therethrough, wherein at least one of the non-fibrous porous layers contains a reagent composition which undergoes a detectable optical change in the presence of a component to be analyzed, which is detectable in the first non-fibrous porous layer and wherein said first non-fibrous porous layer comprises polysulfone.

It is preferable that the reagent composition is contained in the first non-fibrous porous layer.

In another embodiment of the invention, the element comprises a water permeable layer provided between the light transmitting and water impermeable support and the first non-fibrous porous layer, wherein the reagent composition is contained in at least one of the water permeable layer and the non-fibrous porous layers. The water permeable layer may be porous or non-porous, but is preferably non-porous.

It is preferable in this embodiment that the reagent composition is contained in at least one of the water permeable layer or the first non-fibrous porous layer.

BRIEF DESCRIPTION OF THE DRAWING

The FIGURE is a cross-sectional view of the multilayer analytical element prepared in Example 1.

DESCRIPTION OF THE PREFERRED EMBODIMENTS

Figure 1:
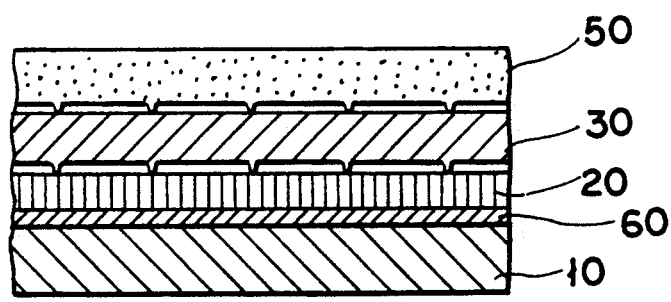

Polysulfone for use in the present invention is a well known resin as described, e.g., in 9285 no kagaku shohin (9285 kinds of chemicals), 665, Kagaku Kogyo Nipposha. The polysulfone which can be used in this invention includes aromatic polysulfone resins and olefinic polysulfone, with the former being preferred. Known aromatic polysulfone resins include a polycondensate of 4,4'-dihydroxydiphenylsulfone, i.e., a polymer having a 4-(4'-oxyphenylenesulfonyl) repeating unit represented by formula (I) shown below, a polymer having a repeating unit of 4,4'-dioxydiphenylsulfone linked with diphenylmethane as represented by formula (II) shown below, and a polymer having a repeating unit of 4,4'-dioxydiphenylsulfone linked with biphenyl as represented by formula (III) shown below.

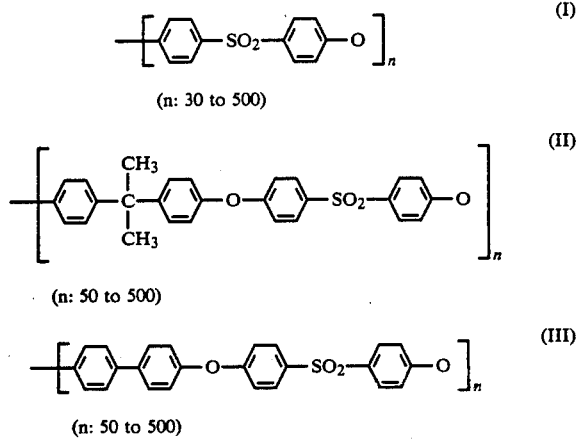

Commercially available polysulfone resins, e.g., Udel Polysulfone (product of Union Carbide, U.S.A. or Nissan Chemicals Industries, Ltd., Japan), Polyether Sulfone (product of I.C.I., Japan), and Astrel (product of Carborandam, U.S.A.), can be used in the present invention.

A fine porous membrane comprising polysulfone can be formed by known processes, e.g., the process described in JP-A-62-27006.

The second non-fibrous porous layer preferably comprises a so-called blush polymer comprising a cellulose ester, e.g., cellulose acetate, cellulose acetate butyrate, and cellulose nitrate, as described in JP-B-53-21677 and U.S. Pat. No. 1,421,341. The fine porous membrane may comprise a polyamide resin, e.g., 6-nylon and 6,6-nylon, polyethylene, or polypropylene. A fine porous membrane comprising polysulfone described in JP-A-62-27006 may also be employed. In addition, a porous layer in which polymer particles, glass particles, diatomaceous earth, etc., are bound with a hydrophilic or non-water-absorbing polymer to form continuous voids may also be used. Of these materials, however, those causing hemolysis are unfavorable because they destroy blood cells in the blood sample and allow hemoglobin to penetrate into the reagent layer.

The thickness of the first and second non-fibrous porous layers may be the same or different and usually ranges from 50 to 500 $\mu$m, and preferably from 80 to 200 $\mu$m.

The first and second non-fibrous porous layers may have the same or different pore sizes. It is preferable, however, that the effective pore size of the first non-fibrous porous layer does not exceed three times the effective pore size of the second non-fibrous porous layer. The second non-fibrous porous layer preferably has an effective pore size of from 0.8 to 30 $\mu$m.

The term "effective pore size" as used herein means a pore diameter as measured by a bubble point method in accordance with ASTM F316-70. When a membrane filter comprising a so-called blush polymer prepared by a phase separation process is used as a non-fibrous porous layer, the passageway for a liquid in the thickness direction is, as a general rule, the narrowest on the free surface side at the time of preparation (i.e., a gloss surface). That is, the cross section of the liquid passageway in the vicinity of the free surface has the smallest circle equivalent pore diameter. Further, the minimum pore size in the thickness direction per unit passageway varies with distribution in the planar direction of the filter, and the maximum value of the sizes (varying with the distribution) determines filtering characteristics. Such a maximum value can be generally determined by a bubble point method.

In a membrane filter comprising a blush polymer prepared by a phase separation process, the liquid passageway is narrowest in the thickness direction at the free surface side thereof (i.e., the gloss surface) as stated above. When this kind of membrane is used as either the first non-fibrous porous layer or the second non-fibrous porous layer, it is preferable to position the gloss surface facing the direction of the support.

The void volume ratios of the first and the second non-fibrous porous layers respectively are usually in the range from 20% to 95%, preferably from 50 to 90%. The void volumes per unit area of the first and the second non-fibrous porous layers respectively are usually 0.4 to 4 cm$^3$ per 100 cm$^2$, preferably 0.5 to 2 cm$^3$ per 100 cm$^2$. The void volume ratio and the void volume per unit area of the fibrous porous layer are in the same ranges as described above as for non-fibrous porous layers:

The second non-fibrous porous layer can be fixed on the first non-fibrous porous layer with an adhesive, but it is necessary that the adhesive not substantially interfere with uniform penetration of a liquid through the layers. To achieve this, the adhesive should be applied locally so that small through-holes of passageways are formed in those areas where adhesive is not applied. This can be done effectively by the method described in JP-A-62-138756. Fixation of the fibrous porous layer on the second non-fibrous porous layer can also be carried out in the same manner.

It is preferable that the void volume of the first non-fibrous porous layer is made smaller than that of the second non-fibrous porous layer. (As used herein, void volume is expressed per unit area) This may be achieved either by making the thickness of the first layer smaller than that of the second layer with the porosity being the same in each or by making the porosity of the first layer smaller than that of the second layer with the thickness of each being the same. The relationship of the void volumes of these two layers may be controlled by an appropriate combination of the thickness and the porosity. It is also possible to use, as the first non-fibrous porous layer, the same material as used for the second non-fibrous porous layer which has been treated with the appropriates solvent so as to reduce its porosity as described.

The analytical element according to the present invention may have various layer structures, for example, a layer structure (1) comprising a support having provided thereon the first non-fibrous porous layer, the second non-fibrous porous layer, and the fibrous porous layer in this order. Included in the scope of the present invention are a layer structure (2) comprising a support having provided thereon an adhesive layer (or water-absorbing layer), the first non-fibrous porous layer, the second non-fibrous porous layer, and the fibrous porous layer in this order; a layer structure (3) comprising a support having provided thereon a detecting layer, the first non-fibrous porous layer, the second non-fibrous porous layer, and the fibrous porous layer in this order; and a layer structure (4) comprising a support having provided thereon a reagent layer (containing a part of a reagent composition), the first non-fibrous porous layer, the second non-fibrous porous layer, and the fibrous porous layer in this order. The support in these structures may have a subbing layer. The details of these layer structures are shown U.S. Pat. No. 3,992,158 and JP-A-55-164356 corresponding to U.S. Pat. No. 4,292,272 and JP-A-62-138756 to 138758.

The detecting layer is a layer where the dye or colored substance, formed in the presence of the component under analysis is diffused and thereby detected optically through the light transmitting support. Generally, it comprises a hydrophilic polymer. The layer structure having such a detecting layer corresponds to the structure according to the embodiment of this invention in which the water permeable layer contains no reagent. The detecting layer may contain a mordant, for example, a cationic polymer mordant for an anionic dye.

The water-absorbing layer is a layer where the dye formed in the presence of the component under analysis is substantially inhibited from diffusion, and generally comprises an easily swelling hydrophilic polymer.

If desired, the analytical element may contain other fibrous or non-fibrous and porous or non-porous layers between the first non-fibrous porous layer and the second non-fibrous porous layer.

If desired, the analytical element may also contain an interferant-removing layer, a gas permeable layer, or a light-reflecting layer between the reagent layer and the first non-fibrous porous layer; or an interferant-removing layer or a light-reflecting layer between the detecting layer and the first non-fibrous porous layer.

A preferred material for the light transmitting and water impermeable support of this invention is polyethylene terephthalate. Cellulose esters, e.g., cellulose triacetate, may also be used. In order to firmly bond a hydrophilic layer to the support, the support is usually subjected to a subbing treatment or treatment for rendering it hydrophilic.

The reagent composition is a composition capable of forming an optically detectable substance, for example, a dye in the presence of the component to be analyzed. That is, the composition contains an indicator which reacts directly with the component under analysis or with an intermediate product formed between the component under analysis and another reagent to thereby form an optically detectable substance, for example, a dye. Included in such a reagent composition are: a composition capable of forming a dye through oxidation of a leuco dye, e.g., arylimidazole leuco dye as disclosed in U.S. Pat. No. 4,089,747 and JP-A-59-193352; a composition containing a diazonium salt or a compound whose oxidation product is capable of forming a dye on coupling with another compound, e.g., 4-aminoantipyrines and phenols or naphthols; and a composition containing a compound capable of forming a dye in the presence of a reduction type coenzyme and an electron transfer agent. In the case of an analytical element for assaying enzymatic activities, a self-developing substrate capable of liberating a colored substance, e.g., p-nitrophenol, can be incorporated into the reagent layer or the spreading layer.

Incorporation of a reagent composition capable of developing a color in the presence of a component to be analyzed into at least one of the non-fibrous porous layers can be carried out, for example, by first applying a solution or dispersion of the reagent composition in an appropriate solvent or medium to a porous spreading layer by impregnation or coating and then bonding the resulting layer onto another water-permeable layer, such as, a reagent layer, in accordance with the method described in JP-A-55-164356 corresponding to U.S. Pat. No. 4,292,272. It may also be effected by first bonding a porous layer onto another water-permeable layer, such as a subbing layer, an adhesive layer, and a water-absorbing layer by the method of JP-A-55-164356 and then coating a solution or dispersion of the reagent composition on the porous layer.

Impregnation or coating of the porous layer with the solution or dispersion of the reagent composition can be carried out by utilizing any known technique. For example, coating can be effected appropriately by dip coating, doctor knife coating, hopper coating, curtain coating, and the like.

The entire quantity of the reagent composition may be incorporated into the first non-fibrous porous layer, or the reagent composition may be divided and individual portions incorporated into the first non-fibrous porous layer and other porous or non-porous layers, such as a reagent layer. For example, a composition which reacts with the component to be analyzed to form an intermediate product is incorporated into the second non-fibrous porous layer, while a composition (indicator) which reacts with the intermediate product to form a dye, etc., is incorporated into the first non-fibrous porous layer.

A part of the reagent composition may also be contained in a non-porous layer comprising a hydrophilic polymer as a binder, e.g., a reagent layer. The hydrophilic polymer to be used includes gelatin and derivatives thereof, e.g., phthalated gelatin, cellulose derivatives, e.g., hydroxyethyl cellulose, agarose, an acrylamide polymer, a methacrylamide polymer, and a copolymer of acrylamide or methacrylamide and various vinyl monomers.

Substantial incorporation of the reagent composition into the first non-fibrous porous layer can be carried out by coating to get a uniform layer containing the reagent composition and the hydrophilic polymer as a binder and then bonding a non-fibrous porous layer containing no reagent composition thereon by the method of JP-A-55-164356.

If desired, the reagent composition can contain additives, such as, an activator, a buffering agent, a hardening agent, and a surface active agent. Examples of the buffering agent which can be added to the reagent layer include carbonates, borates, phosphates, and Good's buffering agents described in *Biochemistry*, Vol. 5, No. 2, 467-477 (1966). These buffering agents can be chosen by referring to literature, e.g., T. Horio, et al., *Tanpakushitsu-Koso no Kiso Jikkenho*, Nankodo (1981) and *Biochemistry*, Vol. 5.

The reagent composition may contain an enzyme. Examples of enzymes which can be used are described in Japanese Patent Application No. 60-279859, 18-20.

Since the fibrous porous layer is utilized as a spreading layer for a liquid sample, it preferably has a liquid metering activity. The term "liquid metering activity" as used herein means the ability of the layer to spread a liquid sample spotted thereon in the planar direction at a substantially constant amount per unit area without causing any substantial localization or separation of the components contained in the liquid sample. Materials which can be used for fibrous porous layer include filter paper, non-woven cloth, woven fabric, such as, plain cloth, knitted fabric, such as, tricot, glass fiber filter, etc., with woven fabric and knitted fabric being preferred. These materials may be subjected to a glow discharge treatment as described in JP-A-57-66359.

The spreading layer can contain a hydrophilic high polymer or a surface active agent as described in JP-A-60-222770 corresponding to EP 0162301A, JP-A-63-219397, 63-112999 and 62-182652 for the purpose of controlling the spreading area and spreading rate.

The fibrous porous layer can be fixed on the non-fibrous porous layer by means of an adhesive. However, it is necessary to assure substantially uniform penetration of a liquid from the fibrous porous layer to the non-fibrous porous layer by locally applying the adhesive so as to form small through-holes in areas where no adhesive is applied. For this purpose, the method described in JP-A-62-138756 can be used.

An adhesive layer for laminate-bonding the non-fibrous porous layer may be provided on the support, the subbing layer, the water-absorbing layer, the detecting layer or the like layer. The adhesive layer preferably comprises a hydrophilic polymer which exhibits adhesion to the porous layer when swollen with water, such as, gelatin, gelatin derivatives, polyacrylamide, starch, etc.

The second non-fibrous porous layer functions to block the red color of hemoglobin in red blood cells and, at the same time, serves as a light-reflective layer or a background layer. Light-reflective particles, e.g., titanium oxide and barium sulfate, dispersed in a hydrophilic polymer may be incorporated into the second non-fibrous porous layer. The hydrophilic polymer used preferably includes gelatin, gelatin derivatives, and polyacrylamide. The light-reflective particles may also be added to either one or both of the first non-fibrous porous layer and the fibrous porous layer.

The present invention is particularly useful for quantitative analyses of not only low-molecular-weight components in whole blood, e.g., urea, uric acid, and creatinine, but also high-molecular-weight components, e.g., total protein, albumin, and various enzymes, as well as hydrophobic components, e.g., cholesterol and glycerides.

The analytical element of the present invention in which an antigen or an antibody is incorporated into one of the porous layer is useful for quantitative determination of the respective antibody or antigen by an immunological assay.

The present invention is now illustrated in greater detail with reference to the following Examples, but it should be understood that the present invention is not deemed to be limited thereto.

EXAMPLE 1

A gelatin aqueous solution was coated onto a 180 μm thick colorless transparent smooth film of polyethylene terephthalate having a gelatin subbing layer and was dried to form a water-absorbing layer having a thickness of 7 μm.

After the surface of the water-absorbing layer was substantially uniformly wetted with water at about 25° C., a 180 μm thick membrane filter of polysulfone having structural formula (II) wherein n is from 50 to 80 and having an effective pore size of 0.4 μm (the effective pore size is defined hereinbefore) which was prepared by the process described in Example 2 of JP-A-62-27006, was superimposed on the water-absorbing layer, followed by drying to bond the membrane filter to the water-absorbing layer.

Then, Composition I and Composition II having the following formulations were coated on the membrane filter in this order and dried to form a porous reagent layer.

| Composition 1: | |
|---|---|
| Gelatin | 0.64 g/m$^2$ |
| Surface active agent (polyoxyethylene nonylphenyl ether) | 2.5 g/m$^2$ |
| Trishydroxymethylaminomethane | 0.46 g/m$^2$ |
| Monopotassium phosphate | 0.46 g/m$^2$ |
| α-Ketoglutaric acid | 0.5 g/m$^2$ |
| Sodium L-aspartate | 2.5 g/m$^2$ |
| Oxaloacetic decarboxylase | 12600 IU/m$^2$ |
| Anhydrous magnesium chloride | 0.3 g/m$^2$ |
| FAD (flavin adenine dinucleotide) | 28 mg/m$^2$ |
| Thiamine pyrophosphate | 35000 IU/m$^2$ |
| Pyruvic oxidase | 6400 IU/m$^2$ |
| Solvent (water) | |
| (pH = 7.5, adjusted with dilute NaOH aqueous solution) | |
| Composition 2: | |
| Leuco dye [2-(3,5-dimethoxy-4-hydroxy phenyl)-4-phenethyl-5-(4-dimethylaminophenyl)imidazole | 1.8 g/m$^2$ |
| Surface active agent (polyoxyethylene (n = 40) nonylphenyl ether) | 0.6 g/m$^2$ |
| Solvent (ethanol) | |

On a cellulose acetate membrane filter having an effective pore size of 3.0 μm (the effective pore size is defined hereinbefore), a thickness of 140 μm, and a porosity of about 80% ("Microfilter FM 300", a product of Fuji Photo Film Co., Ltd.) was applied in an amount of 3 g/m² (as solids) of a starch paste by screen printing using a 100 mesh net (area ratio: about 20%). The membrane filter was then laminated on the porous reagent layer via the starch paste, followed by drying to form a second non-fibrous porous layer.

A tricot knitted fabric having a thickness of about 250 μm of polyethylene terephthalate spun yarns corresponding to 100S was laminate-bonded on the second non-fibrous porous layer by the same spot bonding method described above to obtain a multi-layer analytical element for assaying AST activity.

The analytical element thus prepared is depicted in the drawing wherein the support is 10, the water-absorbing layer is 60, the reagent layer is 20 (first non-fibrous porous layer), the blood cell filtering layer is 30 (second non-fibrous porous layer), and the developing layer is 50 (fibrous porous layer).

EXAMPLE 2

On a 180 μm thick colorless transparent smooth polyethylene terephthalate film having a gelatin subbing layer was coated an aqueous solution having the following composition and dried to form a first reagent layer.

| Composition 3: | |
|---|---|
| Gelatin | 8.2 g/m² |
| Surface active agent (polyoxyethylene (40) nonylphenyl ether) | 0.41 g/m² |
| FAD | 22 mg/m² |
| Thiamine pyrophosphate | 93 mg/m² |
| Pyruvic oxidase | 12300 IU/m² |
| Peroxidase | 6520 IU/m² |
| Bis[(vinylsulfonylmethylcarbonyl)-amino]methane | 180 mg/m² |
| Solvent of the above components (water) | |
| Leuco dye [2-(3,5-dimethoxy-4-hydroxyphenyl)-4-phenethyl-5-(4-dimethylaminophenyl)imidazole | 280 mg/m² |
| Solvent for leuco dye (ethanol) | |
| (pH = 7.5, adjusted with dilute NaOH aqueous solution) | |

After the reagent layer was substantially uniformly wetted with water at about 25° C., a 180 μm thick membrane filter of polysulfone having structural formula of (II) and having an effective pore size of 0.4 μm was superposed on the reagent layer and dried to bond the membrane filter onto the reagent layer.

Composition 4 shown below was then coated on the membrane filter and dried to form a porous reagent layer.

| Composition 4: | |
|---|---|
| Trishydroxymethylaminomethane | 0.30 g/m² |
| Monopotassium phosphate | 0.36 g/m² |
| α-Ketoglutaric acid | 0.32 g/m² |
| Sodium L-aspartate | 1.92 g/m² |
| Oxaloacetic decarboxylase | 12600 IU/m² |
| Anhydrous magnesium chloride | 18.7 g/m² |
| Hydroxypropylmethyl cellulose | 3.2 g/m² |
| (pH = 7.5, adjusted with dilute NaOH aqueous solution) | |

On a cellulose acetate membrane filter having an effective pore size of 3.0 μm, a thickness of 140 μm, and a porosity of about 80% (Microfilter FM 300) was applied in an amount of 3 g/m² (as solids) a starch paste through a 100 mesh net (area ratio: about 20%) by screen printing. The membrane filter was then laminate-bonded on the porous reagent layer via the starch paste, followed by drying to form a second non-fibrous porous layer.

A tricot butted fabric having a thickness of about 250 μm of polyethylene terephthalate spun yarns corresponding to 100S was bonded to the second non-fibrous porous layer by the same spot bonding method described above to obtain a multi-layer analytical element for assaying AST activity.

COMPARATIVE EXAMPLE 1

A multi-layer analytic element was prepared in the same manner as in Example 1, except that a cellulose acetate membrane filter having an effective pore size of 3.0 μm, a thickness of 140 μm, and a porosity of about 80% was used in place of the polysulfone membrane filter.

ANALYSIS EXAMPLE 1

To fresh whole blood having a hematocrit value of 43% (collected by using a heparinized syringe) were added: a blood plasma; blood cells; and AST originating from pig (a product of SIGMA) to prepare a series of blood samples having hematocrit values of 25%, 40% or 55% and an AST activity of 220 unit/l or 856 unit/l (six samples in total).

Each of the analytical elements prepared in Example 1 and 2 and Comparative Example 1 was cut into 1.5×1.5 cm squares, and the cut piece was fitted to a plastic mount having an opening for dropping a sample and an opening for measurement. Each of the 6 samples was dropped onto the element and allowed to react at 37° C. After 2.5 minutes and 4 minutes from the dropping, absorption at 640 nm was measured from the side of the support by reflective photometry, and the result was converted to ODt (transmissive optical density). The AST activity was calculated therefrom according to the theory described in *Clinical Chemistry*, Vol. 24, 1335 (1978). The results obtained are shown in Table 1.

TABLE 1

| Example No. | GOT Concentration (unit/l) | AST Activity Hematocrit Value | | |
|---|---|---|---|---|
| | | 25% | 40% | 55% |
| Example 1 | 220 | 221 | 220 | 212 |
| | 856 | 883 | 852 | 841 |
| Example 2 | 220 | 233 | 221 | 218 |
| | 856 | 887 | 856 | 838 |
| Comparative Example 1 | 220 | 302 | 221 | 135 |
| | 856 | 1026 | 855 | 787 |

As can be seen from the results of Table 1, the AST activity measured with the comparative analytical element is considerably scattered due to a variation of the hematocrit value of the blood, while the analytical elements according to the present invention do not exhibit such scatter. In other words, the analytical elements of the present invention show superior reliability in assaying the enzymatic activities of blood.

EXAMPLE 3

A 180 μm thick colorless transparent and smooth polyethylene terephthalate film having a gelatin subbing layer was coated with an aqueous solution of polyvinyl alcohol having an average degree of polymerization of 1,000 and a degree of saponification of about 88% to a dry thickness of 25 μm. The film dried to form a water-absorbing layer.

After the surface of the water-absorbing layer was substantially uniformly wetted with water at about 25° C., a membrane filter of polysulfone having a structural formula (II) and having an effective pore size of 0.4 μm and a thickness of 180 μm was laminated on the water-absorbing layer and dried to bond the membrane filter onto the water-absorbing layer.

An aqueous solution having the following composition was coated on the membrane filter and dried to form a porous reagent layer.

| Composition 5: | |
|---|---|
| Dyphiline (cf. Merck Index, 10th Ed., 503, item 3465) | 8.0 g/m² |
| Sulfosalicylic acid | 1.6 g/m² |
| 2,4-Dichlorobenzenediazonium sulfosalicylic acid salt | 0.16 g/m² |

The surface of a cellulose acetate membrane having an effective pore size of 3.0 μm, a thickness of 140 μm, and a porosity of about 80% (Microfilter FM 300) was coated with 3 g/m² (as solids) of a starch paste through a 100 mesh net (area ratio: about 20%) by screen printing. The membrane filter was laminate-bonded onto the porous reagent layer via the starch paste, followed by drying to form a second non-fibrous porous layer.

An approximately 250 μm thick tricot knitted fabric comprising polyethylene terephthalate spun yarns corresponding to 100S was then laminate-bonded on the second non-fibrous porous layer by the same spot bonding method as described above to obtain a multi-layer analytical element for the dry quantitative analysis of bilirubin.

COMPARATIVE EXAMPLE 2

A multi-layer analytical element was prepared in the same manner as in Example 3, except that the polysulfone membrane filter used in Example 3 was replaced with a cellulose acetate membrane filter having an effective pore size of 3.0 μm, a thickness of 140 μm, and a porosity of about 80% (Microfilter FM 300).

ANALYSIS EXAMPLE 2

Blood cells separated from fresh human whole blood collected by using a heparinized syringe were added to a serum for monitoring ("Moni-Trol IX" or "Omega Bilirubin" both produced by Dade Co.) to prepare a series artificial blood samples having a hematocrit value of 40% and bilirubin contents of 0.5, 4.5, 10.6 and 18.6 mg/l.

Ten microliters of each of the artificial blood samples were added to each of the analytical elements obtained in Example 3 and Comparative Example 2, and the elements were incubated in a closed container at 37° C. After 6 minutes, the reflective density of the element was measured at a wavelength of 540 nm to obtain the bilirubin content. The results obtained are shown in Table 2 below.

TABLE 2

| Theoretical Value (mg/l) | Measured Value | |
|---|---|---|
| | Example 3 (mg/dl) | Compara. Example 2 (mg/dl) |
| 0.5 | 0.5 | 0.5 |
| 4.5 | 4.6 | 4.5 |
| 10.6 | 10.9 | 10.2 |
| 18.6 | 18.6 | 18.2 |

As is demonstrated by Table 2, the dry analytical element according to the present invention enables the determination of total cholesterol content with high precision.

In order to evaluate the simultaneous reproducibility of the analytical element, the same analysis as described above was repeated 10 times with samples having a bilirubin content of 4.5 mg/l or 10.6 mg/dl. The results obtained are shown in Table 3.

TABLE 3

| Example No. | Theoretical Value (mg/dl) | Mean Value (mg/dl) | Standard Deviation | Coefficient of Variation (%) |
|---|---|---|---|---|
| Example 3 | 4.5 | 4.6 | 0.117 | 2.6 |
| | 10.6 | 10.6 | 0.163 | 1.5 |
| Comparative Example 2 | 4.5 | 4.5 | 0.250 | 5.5 |
| | 10.6 | 10.6 | 0.432 | 4.1 |

REFERENCE EXAMPLE

The light shielding effects of the polysulfone membrane filter used as the first non-fibrous porous layer of the inventive analytical element and a conventionally employed cellulose acetate membrane filter were examined as follows:

Each of the polysulfone membrane filters used in Example 1 (designated A) and a cellulose acetate membrane filter having an effective pore size of 0.8 μm and a thickness of 180 μm (Microfilter FM 80, a product of Fuji Photo Film Co., Ltd.) (designated B), both provided on a support, was impregnated with water.

The reflective optical density (ODr) of the membrane was measured from the side of the support on a black board background or a white board background at a wavelength of 450 to 800 μm, and the difference of the ODr depending on the background was measured. The results obtained are shown in Table 4.

TABLE 4

| Filter | Difference in ODr | |
|---|---|---|
| | Minimum | Maximum |
| A | 0.16 | 0.22 |
| B | 0.57 | 0.63 |

As can be seen from Table 4, filter B causes an optical density difference of from 0.57 to 0.63 between the measurement on a white background and the measurement on a black background, while the difference is reduced to about ⅓, i.e., 0.16 to 0.22, when using filter A.

As described in the foregoing, the analytical elements in accordance with the present invention excludes the influence of the background caused by blood, etc. in the side of the developing layer because of the high light-shielding effect of the first non-fibrous porous layer. The mention achieves improved precision of analysis, and particularly simultaneous reproducibility.

In addition, the analytical element of the present invention is surprisingly free from the influence of the hematocrit value of a blood sample under analysis. That is, the analytical element offers analysis values substantially independent of the hematocrit value which may vary widely from 25% to 55%. Therefore, the present invention does not require consideration of the hematocrit values of samples, thereby increasing the precision of clinical examinations and reducing the time required therefor.

The present invention has been described in detail and with reference to specific embodiments thereof, it will be apparent to one skilled in the art that various changes and modifications can be made therein without departing from the spirit and scope thereof.

While the invention has been described in detail and with reference to specific embodiments thereof, it will be apparent to one skilled in the art that various changes and modifications can be made therein without departing from the spirit and scope thereof.

What is claimed is:

1. A multi-layer analytical element comprising in this order, a light transmitting and water impermeable support, a first non-fibrous porous layer, a second non-fibrous porous layer, and a fibrous porous layer, the three porous layers being locally bonded together with an adhesive to allow for through-holes so as not to substantially interfere with uniform penetration of a liquid therethrough, at least one of the non-fibrous porous layers containing a reagent composition which undergoes a detectable optical change in the presence of a component to be analyzed, said optical change being detectable in the first non-fibrous porous layer, wherein said first non-fibrous porous layer comprises a polysulfone.

2. The multi-layer analytical element as claimed in claim 1 wherein said reagent composition is present in the first non-fibrous porous layer.

3. The multi-layer analytical element as claimed in claim 1 wherein said second non-fibrous porous layer has an effective pore size of from 0.8 to 30 μm.

4. The multi-layer analytical element of claim 1 wherein the effective pore size of the first non-fibrous porous layer is not more than three times the effective pore size of the second non-fibrous porous layer.

5. The multi-layer analytical element of claim 1 wherein the void volume of the first non-fibrous porous layer is less than that of the second non-fibrous porous layer.

6. The multi-layer analytical element of claim 1 wherein an antibody or an antigen is incorporated into one of the porous layers.

7. A multi-layer analytical element comprising in this order, a light transmitting and water impermeable support, a water permeable layer, a first non-fibrous porous layer, a second non-fibrous porous layer, and a fibrous porous layer in this order, the three porous layers being bonded locally together with an adhesive to allow for through-holes so as not to substantially interfere with uniform penetration of a liquid therethrough, at least one of the water permeable layer and non-fibrous porous layers containing a reagent composition which undergoes a detectable optical change in the presence of a component to be analyzed, said optical change being detectable in the water permeable layer, wherein said first non-fibrous porous layer comprises polysulfone.

8. The element of claim 7 wherein said second non-fibrous porous layer has an effective pore size of from 0.8 to 30 μm.

9. The element of claim 7 wherein the reagent composition is contained in the water permeable layer or the first non-fibrous layer.

10. The element of claim 7 wherein the water-permeable layer is porous.

11. The element of claim 7 wherein the water-permeable layer is non-porous.

12. The element of claim 7 wherein the effective pore size of the first non-fibrous porous layer is not more than three times the effective pore size of the second non-fibrous porous layer.

13. The element of claim 7 wherein the void volume of the first non-fibrous porous layer is less than that of the second non-fibrous porous layer.

14. The element of claim 7 wherein an antibody or an antigen is incorporated into one of the porous layers.

15. In a method for the quantitative analysis of components of body fluids wherein a sample of the fluid to be analyzed is spotted onto a dry analytical element and an optical measurement is thereafter performed on the element, the improvement which comprises the element being the analytical element of claim 1.

16. In a method for the quantitative analysis of components of body fluids wherein a sample of the fluid to be analyzed is spotted onto a dry analytical element and an optical measurement is thereafter performed on the element, the improvement which comprises the element being the analytical element of claim 6.

* * * * *